US012778497B2

(12) United States Patent
Tada et al.

(10) Patent No.: US 12,778,497 B2
(45) Date of Patent: Nov. 3, 2026

(54) SYSTEM FOR MONITORING HEALTH STATUS

(71) Applicant: TERUMO KABUSHIKI KAISHA, Tokyo (JP)

(72) Inventors: Yuichi Tada, Santa Clara, CA (US); Yoichiro Kuwano, Machida Tokyo (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 818 days.

(21) Appl. No.: 17/964,002

(22) Filed: Oct. 11, 2022

(65) Prior Publication Data

US 2023/0200726 A1 Jun. 29, 2023

(30) Foreign Application Priority Data

Dec. 28, 2021 (JP) ................................ 2021-214750

(51) Int. Cl.
*A61B 5/0205* (2006.01)
*A61B 5/00* (2006.01)
(Continued)

(52) U.S. Cl.
CPC .......... *A61B 5/4842* (2013.01); *A61B 5/0008* (2013.01); *A61B 5/0022* (2013.01); *A61B 5/01* (2013.01); *A61B 5/02007* (2013.01); *A61B 5/1114* (2013.01); *A61B 5/4875* (2013.01); *A61B 5/6828* (2013.01); *A61B 5/7264* (2013.01); *A61B 5/741* (2013.01);
(Continued)

(58) Field of Classification Search
CPC .......... A61B 5/01; A61B 5/7275; A61B 5/026
See application file for complete search history.

(56) References Cited

U.S. PATENT DOCUMENTS

2003/0163061 A1 8/2003 Miyoshi et al.
2004/0171940 A1 9/2004 Narimatsu
(Continued)

FOREIGN PATENT DOCUMENTS

CN 106164929 A 11/2016
JP H05-23323 A 2/1993
(Continued)

OTHER PUBLICATIONS

Notice of Reasons for Refusal mailed May 13, 2025 in corresponding Japanese Patent Application No. 2021-214750, 10 pages.

*Primary Examiner* — Michael J D'Abreu
(74) *Attorney, Agent, or Firm* — Kim & Stewart LLP

(57) ABSTRACT

A system for monitoring a health status of a person, includes a mobile terminal configured to display the status and in wireless communication with a first sensor attached to one leg of the person to acquire first information relating to a state of the one leg, and a second sensor attached to a part of a body of the person other than said one leg to acquire second information relating to a state of the part, and a server in communication with the terminal to acquire the first and second information from the sensors. The server is configured to compare the first and second information and determine a blood vessel state of said one leg based on its difference, and transmit to the terminal information indicating the blood vessel state. The mobile terminal is configured to update the status based on the information.

17 Claims, 9 Drawing Sheets

(51) Int. Cl.

| | |
|---|---|
| ***A61B 5/01*** | (2006.01) |
| ***A61B 5/02*** | (2006.01) |
| ***A61B 5/11*** | (2006.01) |
| *A61B 5/103* | (2006.01) |

(52) U.S. Cl.

CPC ............ *A61B 5/742* (2013.01); *A61B 5/1032* (2013.01); *A61B 2562/0219* (2013.01); *A61B 2562/0271* (2013.01); *A61B 2562/04* (2013.01)

(56) References Cited

U.S. PATENT DOCUMENTS

| | | | | |
|---|---|---|---|---|
| 2009/0030289 | A1 | 1/2009 | Katayama et al. | |
| 2012/0083696 | A1 | 4/2012 | Kitamura | |
| 2012/0283530 | A1 | 11/2012 | Maynard et al. | |
| 2013/0289394 | A1 | 10/2013 | Hielscher et al. | |
| 2015/0089365 | A1 | 3/2015 | Zhao et al. | |
| 2015/0150457 | A1 | 6/2015 | Wu et al. | |
| 2019/0313913 | A1* | 10/2019 | Fu ............................ | A61B 5/01 |
| 2022/0280034 | A1 | 9/2022 | Soares et al. | |

FOREIGN PATENT DOCUMENTS

| | | | |
|---|---|---|---|
| JP | 2003-245259 | A | 9/2003 |
| JP | 2003-310601 | A | 11/2003 |
| JP | 2004-121616 | A | 4/2004 |
| JP | 2004-261319 | A | 9/2004 |
| JP | 2012-075702 | A | 4/2012 |
| JP | 2013-511341 | A | 4/2013 |
| JP | 2017-501459 | A | 1/2017 |
| WO | 2006/070823 | A1 | 7/2006 |
| WO | 2021-020444 | A1 | 2/2021 |

* cited by examiner

SYSTEM FOR MONITORING HEALTH STATUS

CROSS-REFERENCE TO RELATED APPLICATION(S)

This application is based on and claims the benefit of priority from Japanese patent application No. 2021-214750, filed Dec. 28, 2021, the entire contents of which are incorporated herein by reference.

BACKGROUND OF THE INVENTION

1. Field of the Invention

Embodiments described herein relate generally to a system for monitoring a health status of a person, a non-transitory computer readable medium storing a program for monitoring a health status of a person, and a method for monitoring a health status of a person.

2. Description of the Related Art

One of abnormalities of a blood vessel is calcification in which calcium is deposited in the blood vessel and the blood vessel is hardened. Patients such as those who undergo cardiovascular therapy, are prone to calcification in blood vessels of lower limbs. When the calcification progresses, a serious disease such as arteriosclerosis is more likely to occur. There is a conventional technique for diagnosing a degree of calcification using X-ray computed tomography (CT).

Such a related art technique requires equipment for X-ray CT, and thus it is not easy to detect an abnormality of a blood vessel such as calcification outside a clinic or a hospital. For example, it is not possible to routinely detect such an abnormality of a blood vessel at home or the like of a patient. Therefore, it is possible for an abnormality of a blood vessel to be overlooked and for symptoms to become worse.

SUMMARY OF THE INVENTION

Embodiments provide a system, a computer readable medium storing a program, and a method capable of routinely determining a blood vessel state.

In one embodiment, a system for monitoring a health status of a person includes a mobile terminal configured to display the health status of the person and in wireless communication with a first sensor, which is attached to one leg of the person to acquire first information relating to a state of the one leg of the patient, and a second sensor, which is attached to a part of a body of the person other than said one leg thereof to acquire second information relating to a state of the part of the body of the person. The system further includes a compute server in communication with the mobile terminal to acquire the first and second information from the first and second sensors through the mobile terminal. The compute server is configured to compare the first and second information and determine a blood vessel state of said one leg of the person difference between the first and second based on a information, and transmit to the mobile terminal information indicating the blood vessel state. The mobile terminal is configured to update the health status of the person based on the information received from the compute server.

In one aspect, the first information related to the state of the one leg of the person and the second information related to another part of the person are acquired using the first sensor and the second sensor, the blood vessel state of the leg of the person is determined based on the first information and the second information, and the information on the determined blood vessel state is output. Simply by attaching the first sensor and the second sensor to the person, it is possible to easily determine and notify of the blood vessel state of the leg of the person without requiring large equipment. Therefore, it is possible to routinely determine and notify of the blood vessel state of the leg.

With the configurations described above, it is possible to routinely determine and notify of a blood vessel state of a person. Therefore, when an abnormality of a blood vessel occurs, the abnormality can be detected at an early stage, and the abnormality of the blood vessel can be dealt with at an early stage.

DESCRIPTION OF THE EMBODIMENTS

Hereinafter, embodiments will be described in detail with reference to the drawings.

First Embodiment

Figure 1:
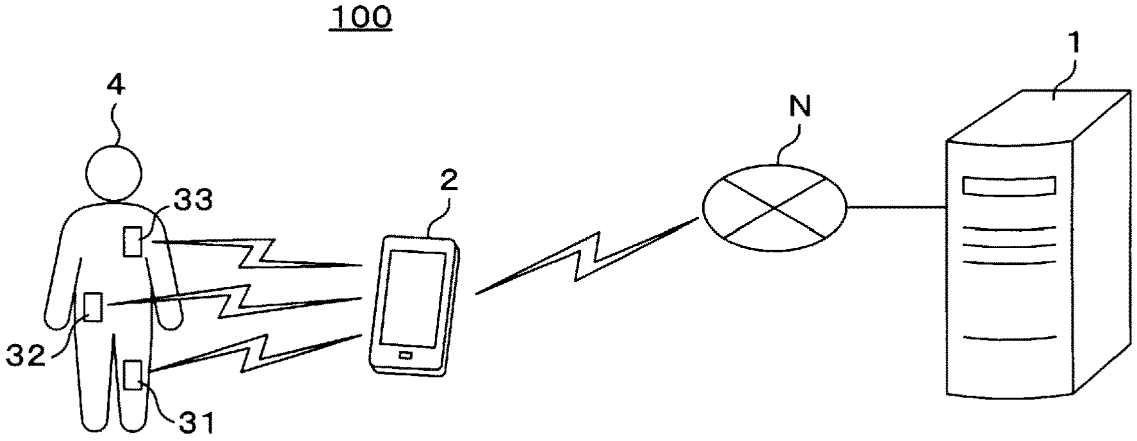
FIG. 1 is a schematic diagram illustrating a configuration of an information output system according to a first embodiment.
Figure 2:
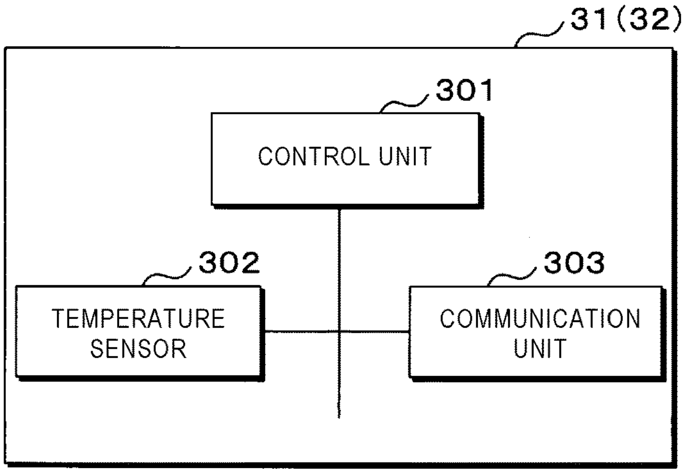
FIG. 2 is a block diagram illustrating an internal configuration of a first sensor and a second sensor.

FIG. 1 is a schematic diagram illustrating a configuration of an information output system 100 according to a first embodiment. The information output system 100 executes an information output method for outputting information on a blood vessel state of a person. The information output system 100 includes a first sensor 31, a second sensor 32, and a third sensor 33 that are attachable to the body of a person 4, a terminal device 2 possessed by the person 4, and an information output device 1. The first sensor 31 is attached to one leg of the person 4, and the second sensor 32 is attached to another part of his or her body other than the one leg of the person 4. The one leg to which the first sensor 31 is attached is a leg that is expected to be in a worse state. For example, the second sensor 32 is attached to the other leg of the person 4. The third sensor 33 may be attached to any part of the body of the person 4. For example, the first sensor 31, the second sensor 32, and the third sensor 33 are routinely attached to the body of the person 4. The first sensor 31, the second sensor 32, and the third sensor 33 transmit information indicating detected values to the terminal device 2. The terminal device 2 receives the information transmitted from the first sensor 31, the second sensor 32, and the third sensor 33, and communicates with the information output device 1 via a communication network N such as the Internet. The terminal device 2 transmits the information transmitted from the first sensor 31, the second sensor 32, and the third sensor 33 to the information output device 1. The information output device 1 outputs information on a blood vessel state of the one leg of the person 4 according to the detected values from the first sensor 31, the second sensor 32, and the third sensor 33. FIG. 2 is a block diagram illustrating an internal configuration of the first sensor 31 and the second sensor 32. The first sensor 31 detects first information related to a state of the one leg of the person 4 to which the first sensor 31 is attached. The first sensor 31 includes a control unit 301, a temperature sensor a 302, and communication unit 303. The control unit 301 is a control circuit or a processor that controls each unit of the first sensor 31. The temperature sensor 302 detects a temperature of a body part to which the first sensor 31 is attached. For example, the temperature sensor 302 measures a temperature of skin of the leg of the person 4 to which the first sensor 31 is attached. The temperature sensor 302 may measure a temperature of air near the leg of the person 4. In this manner, the first sensor 31 detects the temperature of the one leg of the person 4. The communication unit 303 transmits the first information indicating the temperature detected by the temperature sensor 302 to an outside of the first sensor 31 by wireless communication. The control unit 301 causes the communication unit 303 to transmit the first information to the terminal device 2. The temperature sensor 302 repeatedly measures the temperature.

The second sensor 32 detects second information related to a state of the part of the person 4 to which the second sensor 32 is attached. A configuration of the second sensor 32 is the same as the configuration of the first sensor 31 described above. That is, the second sensor 32 includes a control unit 301, a temperature sensor 302, and a communication unit 303. The temperature sensor 302 included in the second sensor 32 detects a temperature of a body part to which the second sensor 32 is attached. In this manner, the second sensor 32 detects a temperature of the body part of the person 4 to which the second sensor 32 is attached. For example, when attached to the other leg of the person 4, the second sensor 32 detects a temperature of the other leg. The communication unit 303 of the second sensor 32 transmits the second information indicating the temperature detected by the temperature sensor 302 to an outside of the second sensor 32 by wireless communication. The control unit 301 of the second sensor 32 causes the communication unit 303 to transmit the second information to the terminal device 2.

Each of the first sensor 31 and the second sensor 32 may include a sensor other than the temperature sensor 302. That is, the first sensor 31 and the second sensor 32 may detect information other than temperatures as first information and second information. For example, each of the first sensor 31 and the second sensor 32 may include a moisture sensor, an odor sensor, or a carbon dioxide sensor. The moisture sensor measures moisture contents of a part of a human body to which the first sensor 31 or the second sensor 32 is attached. The odor sensor detects odor components at a part of a human body to which the first sensor 31 or the second sensor 32 is attached, and measures odor intensities. The carbon dioxide sensor measures amounts of carbon dioxide at a part of a human body to which the first sensor 31 or the second sensor 32 is attached. The first information and the second information indicate the moisture contents, the odor intensities, or the amounts of carbon dioxide. Each of the first sensor 31 and the second sensor 32 may include a color sensor that measures colors of skin of a part of a human body to which the first sensor 31 or the second sensor 32 is attached. The first sensor 31 and the second sensor 32 may include a plurality of sensors and transmit, to the terminal device 2, the first information and the second information measured by the plurality of sensors.

Figure 3:
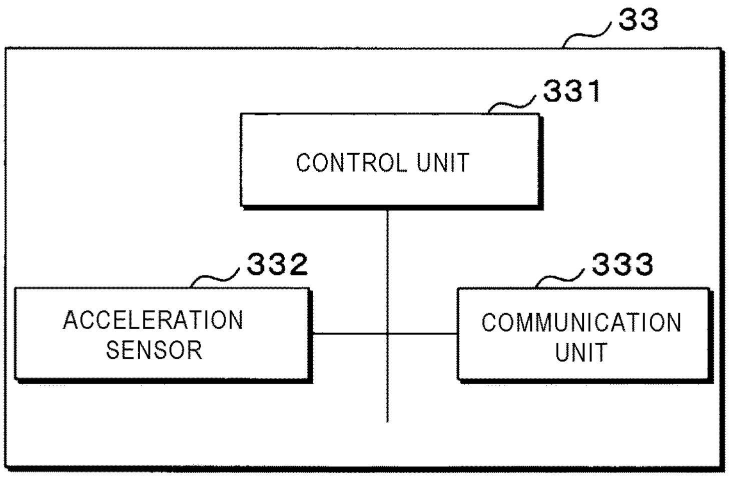
FIG. 3 is a block diagram illustrating an internal configuration of a third sensor.

FIG. 3 is a block diagram illustrating an internal configuration of the third sensor 33. The third sensor 33 is attached to the body of the person 4, and detects third information indicating an amount of change in motion of the person 4 compared to a rest state of the person 4. The third sensor 33 includes a control unit 331, an acceleration sensor 332, and a communication unit 333. The control unit 331 is a control circuit or a processor that controls each unit of the third sensor 33. The acceleration sensor 332 measures an acceleration thereof. Measured accelerations are different between a moving state of the person 4 and a rest state of the person 4. A state of the person 4 may be determined to be a moving state or a rest state according to the measured acceleration. The communication unit 333 transmits the third information indicating the acceleration detected by the acceleration sensor 332 to an outside of the third sensor 33 by wireless communication. The control unit 331 causes the communication unit 333 to transmit the third information to the terminal device 2. The acceleration sensor 332 measures the repeatedly acceleration.

The third sensor 33 may include a sensor other than the acceleration sensor 332. That is, the third sensor 33 may detect information other than the acceleration as the third information. For example, the third sensor 33 may include a heart rate sensor that measures a heart rate of the person 4. The third information indicates the heart rate. The third sensor 33 may include a plurality of sensors and transmit, to the terminal device 2, the third information indicating a plurality of types of amounts measured by the plurality of sensors.

The first sensor 31, the second sensor 32, and the third sensor 33 are preferably secured to the body of the person 4. For example, the first sensor 31, the second sensor 32, and the third sensor 33 are parts of clothes or accessories. For example, the first sensor 31, the second sensor 32, and the third sensor 33 are parts of shoes, socks, tights, rings, or implants. The first sensor 31, the second sensor 32, and the third sensor 33 may be attached to or adhered to the body of the person 4 using belts. The first sensor 31, the second sensor 32, and the third sensor 33 may be housed in pockets of clothes. The third sensor 33 may be integrated with the first sensor 31 or the second sensor 32.

Figure 4:
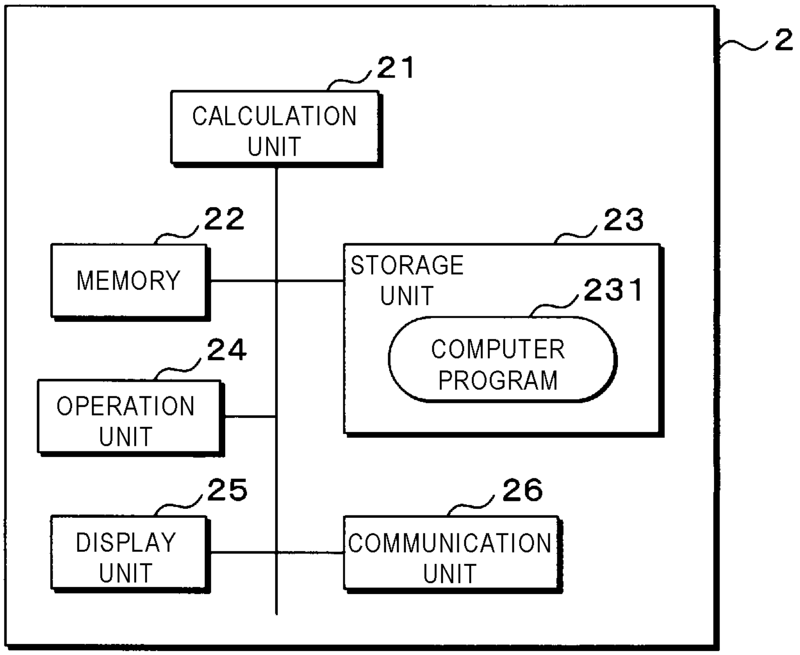
FIG. 4 is a block diagram illustrating an internal configuration of a terminal device.

FIG. 4 is a block diagram illustrating an internal configuration of the terminal device 2. The terminal device 2 is a portable computer such as a smart phone or a tablet computer. For example, the terminal device 2 is a mobile phone or computer owned by the person 4. The terminal device 2 includes a calculation unit 21, a memory 22, a storage unit 23, an operation unit 24, a display unit 25, and a communication unit 26. The calculation unit 21 is a processor such as a central processing unit (CPU), a graphics processing unit (GPU), or a multi-core CPU. The calculation unit 21 may be a quantum processor. The memory 22 stores temporary data generated along with calculation. The memory 22 is, for example, a random access memory (RAM). The storage unit 23 is nonvolatile, and is, for example, a hard disk or a nonvolatile semiconductor memory. The operation unit 24 receives an input operation such as a text input by the person 4. The operation unit 24 is, for example, a touch panel. The display unit 25 displays an image. The display unit 25 may be, for example, a liquid crystal display (LCD) or an electroluminescent (EL) display. The operation unit 24 and the display unit 25 may be integrated into a touch display. The communication unit 26 is a network interface circuit that receives information transmitted from the first sensor 31, the second sensor 32, and the third sensor 33 by wireless communication. In addition, the communication unit 26 communicates with the information output device 1 via the communication network N by wireless communication.

The storage unit 23 stores a computer program 231.

The computer program 231 is downloaded using the communication unit 26 and stored in the storage unit 23. For example, the computer program 231 is downloaded from the information output device 1. The computer program 231 may be stored in the storage unit 23 in advance.

Alternatively, the computer program 231 may be stored in the memory 22 instead of the storage unit 23. For example, the computer program 231 may be downloaded when a process related to the information output system 100 is executed, stored in the memory 22, and deleted from the memory 22 when the process related to the information output system 100 is ended. The calculation unit 21 executes necessary processes according to the computer program 231.

Figure 5:
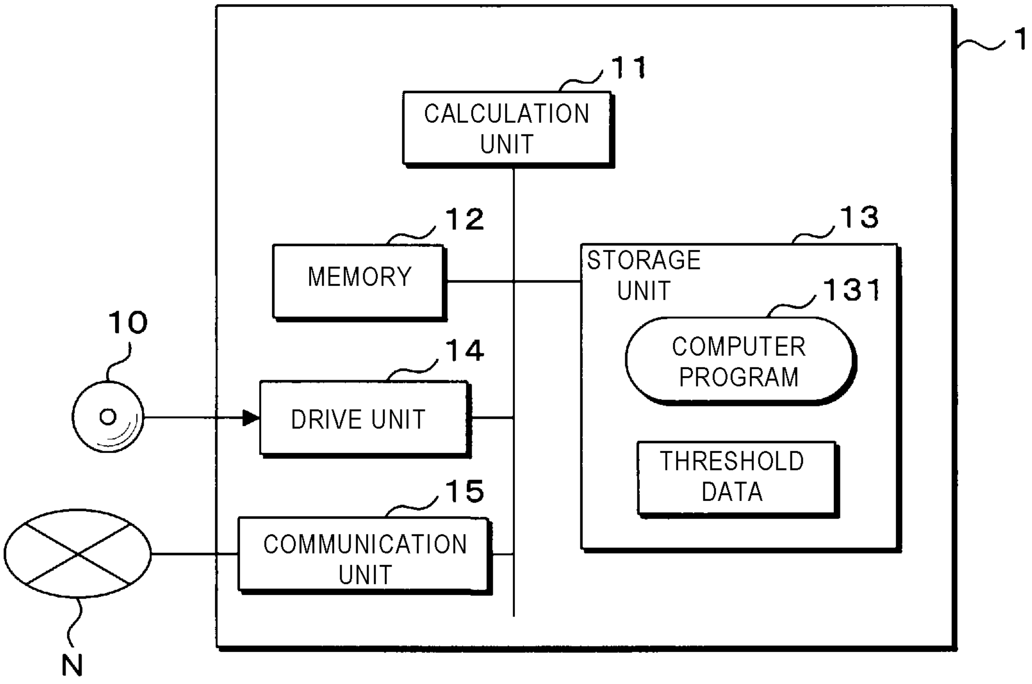
FIG. 5 is a block diagram illustrating an internal functional configuration of an information output device according to the first embodiment.

FIG. 5 is a block diagram illustrating an internal functional configuration of the information output device 1 according to the first embodiment. The information output device 1 is implemented by a computer such as a compute server. The information output device 1 includes a calculation unit 11, a memory 12 that stores temporary data generated along with calculation, a storage unit 13, a drive unit 14 that reads information from a recording medium 10 such as an optical disk or a portable memory, and a communication unit 15. The calculation unit 11 is a processor such as a CPU, a GPU, or a multi-core CPU. The calculation unit 11 may be a quantum processor. The memory 12 is, for example, a RAM. The storage unit 13 is nonvolatile, and is, for example, a hard disk. The communication unit 15 is a network interface circuit connectable to the communication network N. The communication unit 15 communicates with the terminal device 2 via the communication network N.

The calculation unit 11 causes the drive unit 14 to read a computer program 131 recorded in the recording medium 10, and causes the storage unit 13 to store the read computer program 131. The calculation unit 11 executes necessary processes for the information output device 1 according to the computer program 131. The computer program 131 may be downloaded from outside of the information output device 1 by the communication unit 15. In this case, the information output device 1 may not include the drive unit 14. The information output device 1 may be implemented by a plurality of computers.

Figure 6:
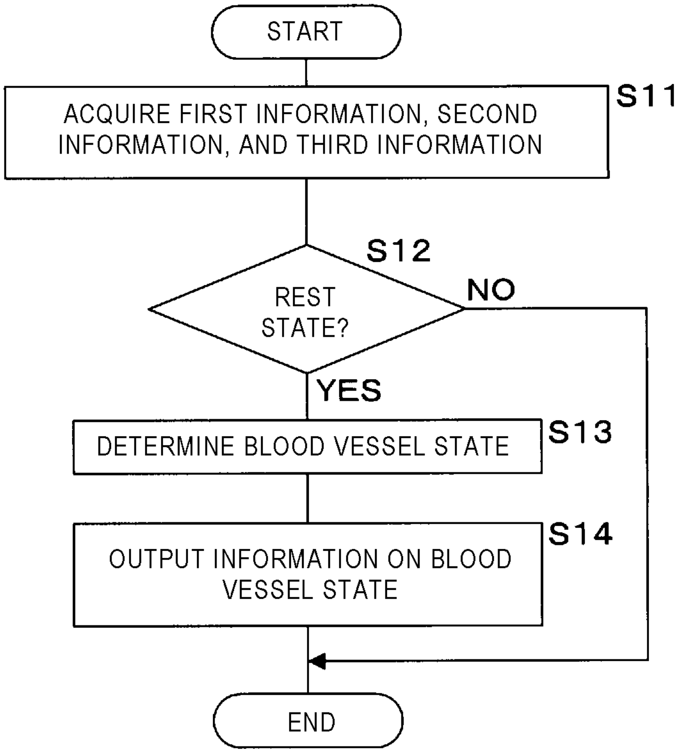
FIG. 6 is a flowchart of an information output process executed by the information output system according to the first embodiment.

The information output system 100 executes a process of outputting information on a blood vessel state of the leg of the person 4 according to information detected by the first sensor 31, the second sensor 32, and the third sensor 33. FIG. 6 is a flowchart of an information output process executed by the information output system 100 according to the first embodiment. Hereinafter, the description of "step" will be abbreviated as "S". The calculation unit 21 of the terminal device 2 executes the following process according to the computer program 231. The calculation unit 11 of the information output device 1 executes the following process according to the computer program 131.

The information output device 1 acquires first information, second information, and third information from the first sensor 31, the second sensor 32, and the third sensor 33, respectively (S11). Specifically, in S11, the first sensor 31 transmits the first information indicating a temperature measured by the temperature sensor 302 to the terminal device 2, the second sensor 32 transmits the second information indicating a temperature measured by the temperature sensor 302 to the terminal device 2, and the third sensor 33 transmits the third information indicating an acceleration measured by the acceleration sensor 332 to the terminal device 2. The terminal device 2 receives the first information, the second information, and the third information via the communication unit 26. The calculation unit 21 of the terminal device 2 causes the communication unit 26 to transmit the received first information, second information, and third information to the information output device 1 via the communication network N. The information output device 1 receives the first information, the second information, and the third information at the communication unit 15. The information output device 1 may store the first information, the second information, and the third information acquired at S11 in the storage unit 13, and may store histories of the acquired first information, second information, and third information in the storage unit 13.

The information output device 1 determines whether the state of the person 4 is the rest state based on the third information (S12). In S12, the calculation unit 11 determines whether the state of the person 4 is the rest state based on the acceleration indicated by the third information. For example, when an absolute value of the acceleration indicated by the third information is equal to or less than a predetermined reference value, the calculation unit 11 determines that the state of the person 4 is the rest state. The reference value is stored in the storage unit 13 in advance, or is included in the computer program 131. In the rest state, the absolute value of the acceleration generated in the person 4 is smaller than the moving state, and thus it is possible to determine that the state of the person 4 is the rest state based on whether the absolute value of the acceleration is smaller than the reference value. The calculation unit 11 may determine based on a single piece of the third information, or may determine based on an average value of a plurality of pieces of the third information acquired within a predetermined length of time.

In S12, for example, the calculation unit 11 may determine whether the state of the person 4 is the rest state based on change in the acceleration indicated by the third information. For example, when an absolute value of a difference in a plurality of accelerations indicated by a plurality of pieces of the third information is equal to or less than a predetermined reference value, the calculation unit 11 determines that the state of the person 4 is the rest state. In the rest state, the change in the accelerations is small, and thus it is possible to determine that the state of the person 4 is the rest state based on whether the change in the accelerations is smaller than the reference value.

When the third information is information other than the acceleration, in S12, the calculation unit 11 can determine whether the state of the person 4 is the rest state based on the third information. For example, when the third information indicates a heart rate and the heart rate is equal to or less than a predetermined reference value, the calculation unit 11 determines that the state of the person 4 is the rest state. When the third information indicates a plurality of pieces of different information measured by a plurality of sensors, the calculation unit 11 may determine whether the state of the person 4 is the rest state based on the plurality of pieces of different information indicated by the third information.

When the state of the person 4 is not the rest state (S12: NO), the information output device 1 ends the process. When the state of the person 4 is the rest state (S12: YES), the information output device 1 determines a blood vessel state of the leg of the person 4 based on the first information and the second information (S13). In S13, the calculation unit 11 uses the first information and the second information acquired substantially simultaneously with the third information which is a basis for determining that the state of the person 4 is the rest state. For example, the calculation unit 11 uses the first information and the second information acquired at a time closest to a time point at which the third information is acquired. For example, time points detected by the first sensor 31, the second sensor 32, and the third sensor 33 are included in or added to the first information, the second information, and the third information, and the calculation unit 11 uses the first information and the second information detected at a time closest to a time point at which the third information is detected.

In S13, the calculation unit 11 calculates a difference in temperatures indicated by the first information and the second information, and compares the calculated difference with a predetermined threshold. The predetermined threshold is stored in the storage unit 13 in advance, or is included in the computer program 131. The calculation unit 11 determines that the blood vessel of the leg to which the first sensor 31 is attached is abnormal when the temperature indicated by the first information is lower than the temperature indicated by the second information and the absolute value of the difference in the temperatures indicated by the first information and the second information exceeds the predetermined threshold. Generally, when calcification occurs in a blood vessel, the blood vessel becomes narrow, and a blood flow is reduced. When the blood flow is reduced due to the abnormality of the blood vessel such as the calcification, a body temperature drops around the abnormal blood vessel. Therefore, when the temperature detected by the first sensor 31 attached to the leg of the person 4 is lower than the temperature detected by the second sensor 32 attached to another part and the absolute value of the difference in the temperatures exceeds the predetermined threshold, it is possible to determine that the blood vessel of the leg is abnormal.

When the second sensor 32 is attached to the other leg of the person 4, in S13, the calculation unit 11 may determine a blood vessel state of the leg to which the second sensor 32 is attached. The calculation unit 11 determines that the blood vessel of the leg to which the second sensor 32 is attached is abnormal when the temperature indicated by the second information is lower than the temperature indicated by the first information and the absolute value of the difference in the temperatures indicated by the first information and the second information exceeds the predetermined threshold.

In S13, the calculation unit 11 determines a degree of abnormality of the blood vessel as the blood vessel state of the leg of the person 4 according to the difference in the temperatures indicated by the first information and the second information. For example, a plurality of thresholds are determined according to a plurality of degrees of abnormality of the blood vessel, and the storage unit 13 stores threshold data in which the thresholds and the degrees of abnormality of the blood vessel are recorded in association with each other. When the abnormality of the blood vessel becomes more severe, for example, when the calcification progresses more, the blood flow is further reduced, and the body temperature significantly drops. Therefore, the threshold increases as the degree of abnormality of the blood vessel becomes severe. In S13, the calculation unit 11 compares the threshold recorded in the threshold data and the difference in the temperatures, and determines, when the absolute value of the difference in the temperatures exceeds a threshold associated with a certain degree and is equal to or less than a threshold associated with a more severe degree, the certain degree as the degree of abnormality of the blood vessel.

More specifically, in S13, the calculation unit 11 determines a progress degree of calcification as the blood vessel state of the leg of the person 4 according to the difference in the temperatures indicated by the first information and the second information. The body temperature significantly drops as the progress degree of calcification is more severe. Therefore, the threshold increases as the progress degree of calcification becomes severe. In S13, the calculation unit 11 compares the threshold recorded in the threshold data and the difference in the temperatures, and determines, when the absolute value of the difference in the temperatures exceeds a threshold associated with a certain progress degree and is equal to or less than a threshold associated with a more severe progress degree, the certain progress degree as the progress degree of calcification of the blood vessel.

In S13, the calculation unit 11 may determine the blood vessel state of the leg of the person 4 according to a medical history of the person 4. Ease of progress of the abnormality of the blood vessel varies depending on the medical history of the person 4. For example, in the case cardiovascular therapy, of the person 4 undergoing calcification is likely to occur in blood vessels of his or her legs. In the threshold data, thresholds are recorded for each medical history such as a treatment history such as cardiovascular therapy, a disease history such as diabetes, smoking status, and health diagnosis data such as body mass index (BMI). For example, in association with a medical history in which an abnormality of a blood vessel such as calcification easily progresses, a threshold smaller than a threshold associated with another medical history is recorded. For example, the medical history of the person 4 is stored in advance in the storage unit 13 in association with identification information of the person 4. In S11, the information output device 1 acquires the identification information of the person 4 together with the first information, the second information, and the third information. In S13, the calculation unit 11 identifies the medical history of the person 4 according to the identification information, and determines the blood vessel state using a threshold corresponding to the identified medical history.

In S13, the calculation unit 11 can determine the blood vessel state of the leg of the person 4 based on first information and second information other than temperatures. For example, when the first information and the second information indicate moisture contents, the calculation unit 11 determines the blood vessel state of the leg of the person 4 according to a difference in the moisture contents indicated by the first information and the second information. When an abnormality of a blood vessel such as calcification occurs, the blood flow is reduced, and a part becomes dry. When the first sensor 31 is attached to a body part near the abnormal blood vessel, the calculation unit 11 calculates the difference in the moisture contents indicated by the first information and the second information, and determines that the blood vessel of the leg to which the first sensor 31 is attached is abnormal when the moisture content indicated by the first information is smaller than the moisture content indicated by the second information and the absolute value of the difference in the moisture contents exceeds a predetermined threshold.

When the first information and the second information indicate odor intensities, the calculation unit 11 determines the blood vessel state of the leg of the person 4 according to a difference in the odor intensities indicated by the first information and the second information. When an abnormality of a blood vessel such as calcification occurs, the blood flow is reduced, necrosis of cells progresses, and a foul odor is generated. Therefore, when an odor intensity detected by the first sensor 31 attached to the leg of the person 4 is larger than an odor intensity detected by the second sensor 32 and the absolute value of the difference in the odor intensities exceeds a predetermined threshold, it is possible to determine that the blood vessel of the leg is abnormal. The calculation unit 11 calculates a difference in the odor intensities indicated by the first information and the second information, and determines that the blood vessel of the leg to which the first sensor 31 is attached is abnormal when the odor intensity indicated by the first information is larger than the odor intensity indicated by the second information and the absolute value of the difference in the odor intensities exceeds a predetermined threshold. When the abnormality of the blood vessel becomes more severe, the blood flow is further reduced, and the odor intensity is further increased. Therefore, the threshold increases as the degree of abnormality of the blood vessel becomes severe.

When the first information and the second information indicate the amounts of carbon dioxide, the calculation unit 11 determines the blood vessel state of the leg of the person 4 according to a difference in the amounts of carbon dioxide indicated by the first information and the second information. A generation amount of carbon dioxide increases as the body temperature increases. When an abnormality of a blood vessel such as calcification occurs, the blood flow is reduced, the body temperature drops, and the generation amount of carbon dioxide decreases. Therefore, when an amount of carbon dioxide detected by the first sensor 31 attached to the leg of the person 4 is smaller than an amount of carbon dioxide detected by the second sensor 32 and the absolute value of the difference in the amounts of carbon dioxide exceed a predetermined threshold, it is possible to determine that the blood vessel of the leg is abnormal. The calculation unit 11 calculates the difference in the amounts of carbon dioxide indicated by the first information and the second information, and determines that the blood vessel of the leg to which the first sensor 31 is attached is abnormal when the amount of carbon dioxide indicated by the first information is smaller than the amount of carbon dioxide indicated by the second information and an absolute value of the difference in the amounts of carbon dioxide exceeds a predetermined threshold. When the abnormality of the blood vessel becomes more severe, the body temperature further drops, and the amount of carbon dioxide further decreases. Therefore, the threshold increases as the degree of abnormality of the blood vessel becomes severe.

When the first information and the second information indicate colors of skin, the calculation unit 11 determines the blood vessel state of the leg of the person 4 according to a difference in the colors of skin indicated by the first information and the second information. When an abnormality of a blood vessel such as calcification occurs, the blood flow is reduced, the body temperature drops, and the color of skin becomes white. Therefore, when a color of skin detected by the first sensor 31 attached to the leg of the person 4 is whiter than a color of skin detected by the second sensor 32 and the absolute value of the difference in the colors of skin exceeds a predetermined threshold, it is possible to determine that the blood vessel of the leg is abnormal. The calculation unit 11 calculates a difference in the colors of skin indicated by the first information and the second information, and determines that the blood vessel of the leg to which the first sensor 31 is attached is abnormal when the color of skin indicated by the first information is whiter than the color of skin indicated by the second information and the absolute value of the difference in the colors of skin exceeds a predetermined threshold. When the abnormality of the blood vessel becomes more severe, the blood flow is further reduced, and the color of skin becomes whiter. Therefore, the threshold increases as the degree of abnormality of the blood vessel becomes severe.

When the second sensor 32 is attached to the other leg of the person 4 and the first information and the second information are information other than temperatures, the calculation unit 11 can determine the blood vessel state of the leg to which the second sensor 32 is attached. When the first information and the second information are information other than temperatures, the calculation unit 11 can determine the degree of abnormality of the blood vessel or the progress degree of calcification of the blood vessel according to a difference in values indicated by the first information and the second information. When the first information and the second information are information other than temperatures, the calculation unit 11 can determine the blood vessel state using the medical history of the person 4.

When each of the first sensor 31 and the second sensor 32 includes a plurality of sensors, the information output device 1 may execute the processing of S13 using the first information and the second information indicating values measured by the plurality of sensors. For example, in S13, the calculation unit 11 determines the blood vessel state of the leg of the person 4 using each of a plurality of types of values such as temperatures, moisture contents, odor intensities, amounts of carbon dioxide, or colors of skin. The calculation unit 11 can determine that the blood vessel is abnormal when an abnormality of the blood vessel is determined using any of such values. The calculation unit 11 can determine that the blood vessel is abnormal when the abnormality of the blood vessel is determined a predetermined number of times or more as a result of the determination using the plurality of types of values.

In S13, the information output device 1 may determine the blood vessel state of the leg of the person 4 based on the first information and the second information measured a plurality of times. For example, the processing of S11 may be repeated a plurality of times, and in S13, the calculation unit 11 may determine based on an average value of a plurality of pieces of the first information and an average value of a plurality of pieces of the second information acquired within a predetermined length of time. For example, the calculation unit 11 may determine based on a minimum value or a maximum value of the plurality of pieces of first information and a minimum value or a maximum value of the plurality of pieces of second information. For example, in S11, the first sensor 31 and the second sensor 32 may transmit the average values of the first information and the second information measured within the predetermined length of time to the information output device 1. In S13, the calculation unit 11 may determine based on the acquired average values of the first information and the second information.

After S13 is ended, the information output device 1 outputs information on the determined blood vessel state (S14). In S14, the calculation unit 11 causes the communication unit 15 to transmit the information on the blood vessel state determined in S13 to the terminal device 2 via the communication network N. In S14, the information output device 1 transmits the information to the terminal device 2 that is a transmission source of the first information and the second information. The terminal device 2 receives the information on the blood vessel state at the communication unit 26, and the calculation unit 21 controls the display unit 25 to display a screen image including the information on the blood vessel state.

Figure 7:
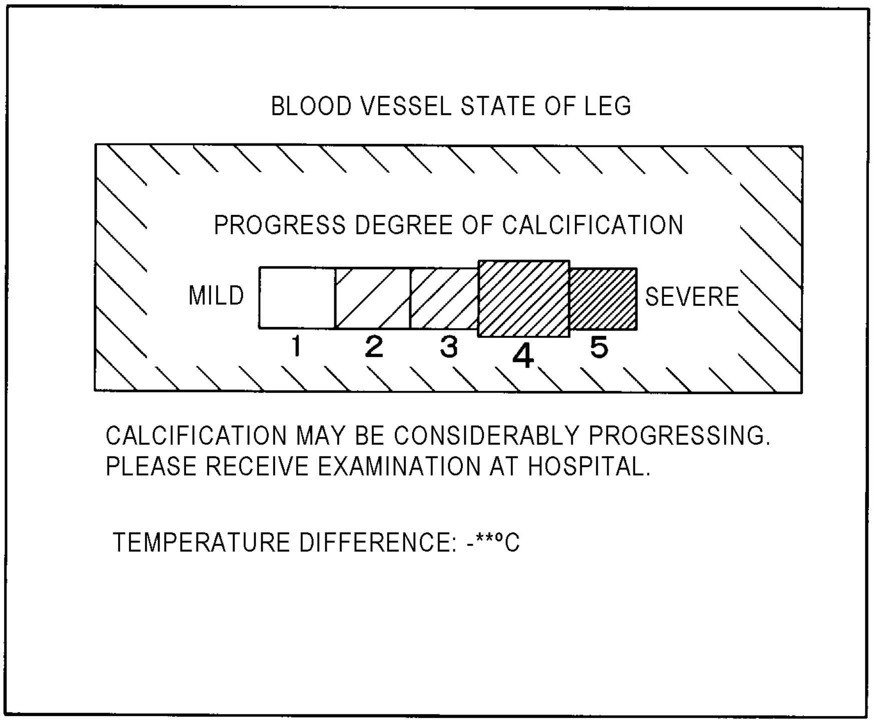
FIG. 7 is a schematic diagram illustrating a first example of a screen image showing information on a blood vessel state.

FIG. 7 is a schematic diagram illustrating a first example of the screen image showing the information on the blood vessel state on the display unit 25. The information illustrating the determined blood vessel state of the leg is included in the image and is output. When no abnormality of the blood vessel is present, information indicating that no abnormality is present is output. When it is determined that the blood vessel is abnormal, information indicating that the blood vessel is abnormal is output. When the degree of abnormality of the blood vessel or the progress degree of calcification of the blood vessel is determined, the degree of abnormality of the blood vessel or the progress degree of calcification of the blood vessel is output. FIG. 7 illustrates an example in which the progress degree of calcification of the blood vessel is output and the progress degree of calcification is a fourth out of five stages.

The information output device 1 executes processing of outputting an image having different colors according to the degree of abnormality degree of calcification of the blood vessel. In S14, the calculation unit 11 generates image data that represents an image having a color corresponding to the degree of abnormality or the progress degree of calcification of the blood vessel and for notifying of the degree of abnormality or the progress degree of calcification of the blood vessel. For example, the image data that represents an image colored blue when the degree of abnormality or the progress degree of calcification of the blood vessel is mild, yellow when moderate, and red when severe is generated. The information output device 1 transmits the image data to the terminal device 2, and the terminal device 2 displays the image on the display unit 25 based on the image data. The information output device 1 may transmit the information indicating the degree of abnormality or the progress degree of calcification of the blood vessel to the terminal device 2 and generate the image having the color corresponding to the degree of abnormality or the progress degree of calcification of the blood vessel on the terminal device 2. The information output device 1 executes processing of outputting advice information corresponding to the determined blood vessel state of the leg. In S14, the calculation unit 11 generates the advice information corresponding to the determined blood vessel state of the leg. For example, text data corresponding to the blood vessel state is recorded is stored in advance in the storage unit 13, and the calculation unit 11 generates the advice information by converting the text data to voice data corresponding to the determined blood vessel state of the leg from the data. The information output device 1 transmits the generated advice information from the communication unit 15 to the terminal device 2, and the terminal device 2 displays an image including the advice information on the display unit 25. The information output device 1 may execute processing of outputting advice information corresponding to the degree of abnormality or the progress degree of calcification of the blood vessel. FIG. 7 illustrates an example in which advice information indicating an advice of recommending receiving a medical examination at a hospital is output.

The information output device 1 executes processing of outputting information on the body of the person 4 using the first sensor 31 and the second sensor 32. In S14, the information output device 1 transmits information representing the difference in the values indicated by the first information and the second information to the terminal device 2, and the terminal device 2 displays an image including the difference in the values indicated by the first information and the second information on the display unit 25. FIG. 7 illustrates an example in which the difference in temperatures is output. In S14, the first information or the second information may be output. A difference in moisture contents, a difference in odor intensities, a difference in amounts of carbon dioxide, or a difference in colors of skin may be output.

Figure 8:
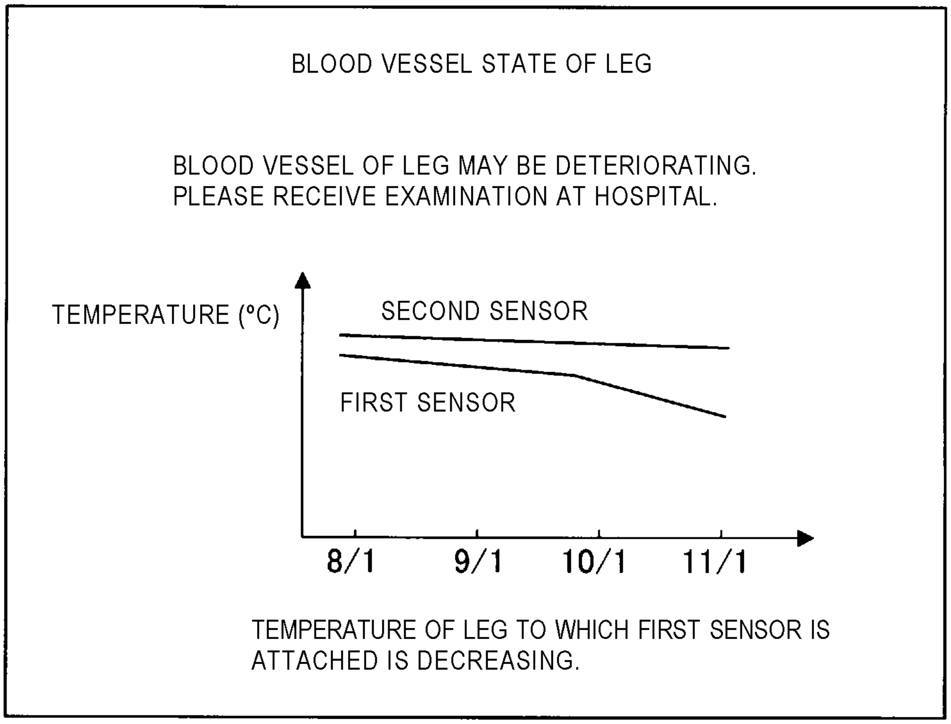
FIG. 8 is a schematic diagram illustrating a second example of the screen image showing the information on the blood vessel state.

FIG. 8 is a schematic diagram illustrating a second example of the screen image showing the information on the blood vessel state. "BLOOD VESSEL OF LEG IS DETERIORATING" is output as advice information corresponding to a blood vessel state of the leg. FIG. 8 illustrates an example in which the image displayed on the display unit 25 includes a graph indicating temporal changes of the first information and the second information. A horizontal axis of the graph in the image represents time, and a vertical axis represents the temperatures measured using the first sensor 31 and the second sensor 32. In S14, the information output device 1 generates the graph based on the histories of the first information and the second information, which are stored in the storage unit 13, and transmits data representing the graph to the terminal device 2. The terminal device 2 displays the image including the graph on the display unit 25.

In the example illustrated in FIG. 8, the temperature measured by the first sensor 31, that is, the temperature of the one leg of the person 4 is lower than the temperature measured by the second sensor; and a temperature difference increases with time. Therefore, it is likely that the blood vessel state of the one leg of the person 4 gradually deteriorates and the calcification progresses. In temporal change in moisture contents, odor S14, a intensities, amounts of carbon dioxide, or colors of skin may be output. Alternatively, a temporal change in the difference between the first information and the second information may be output. For example, a temporal change in the difference in the temperatures measured using the first sensor 31 and the second sensor 32 may be output. A temporal change in the differences of the moisture contents, the differences of the odor intensities, the differences of the amounts of carbon dioxide, or the differences of the colors of skin may be output.

Figure 9:
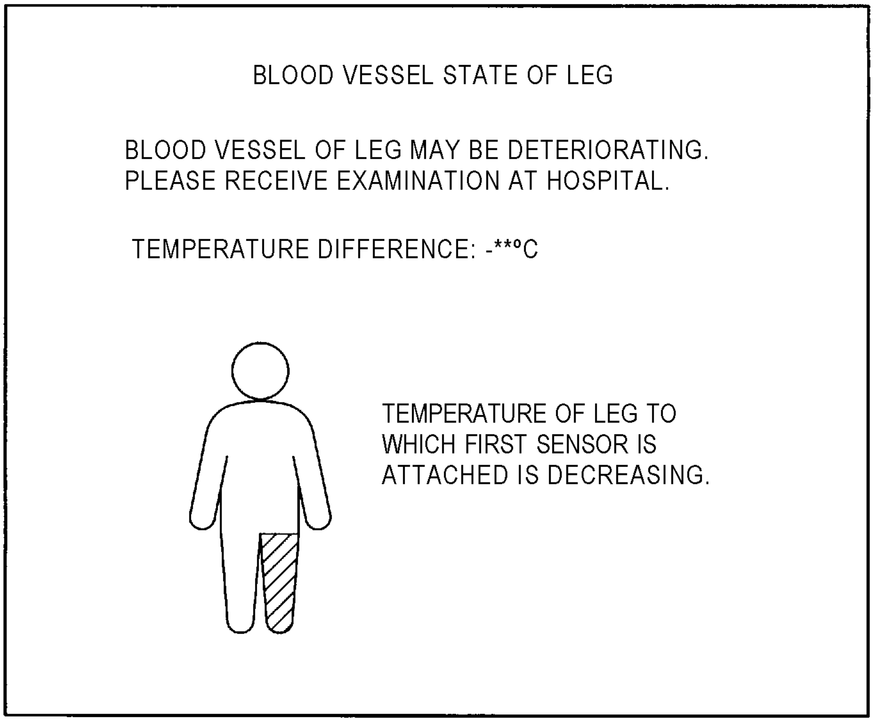
FIG. 9 is a schematic diagram illustrating a third example of the screen image showing the information on the blood vessel state.

FIG. 9 is a schematic diagram illustrating a third example of the screen image showing the information on the blood vessel state. "BLOOD VESSEL OF LEG IS DETERIORATING" is output as advice information corresponding to the blood vessel state of the leg. FIG. 9 illustrates an example in which a human-shaped figure is displayed and a color of a leg of the human-shaped figure is changed. For example, when the temperature measured by the first sensor 31, that is, the temperature of the one leg of the person 4 is lower than the temperature measured by the second sensor 32, the color of the leg of the human-shaped figure is set to a particular color, e.g., blue. For example, when the temperature of the one leg of the person 4 is higher than the temperature measured by the second sensor 32, the color of the leg of the human-shaped figure is set to a warmer color, e.g., orange.

In S14, the terminal device 2 displays, on the display unit 25, an image including the human-shaped figure in which the color of the leg is changed based on the difference between the values indicated by the first information and the second information. Alternatively, the information output device 1 generates the human-shaped figure in which the color of the leg is changed based on the difference in the values indicated by the first information and the second information, and transmits data representing the figure to the terminal device 2. The terminal device 2 displays the image including the figure on the display unit 25. The color of the leg of the human-shaped figure is changed, and thus it is easy for the person 4 to know the abnormality potentially occurred in his or her leg. For example, the color of the leg of the human-shaped figure is changed to blue, and thus it is easy for the person 4 to confirm that a temperature of the leg of the person 4 drops and the blood vessel of the leg is abnormal. In S14, the color of the leg of the human-shaped figure may be changed according to a difference in moisture contents, a difference in odor intensities, a difference in amounts of carbon dioxide, or a difference in colors of skin. The images illustrated in FIGS. 7 to 9 may be output in combination.

After S14 is ended, the information output system 100 ends the process of outputting the information on the blood vessel state of the leg of the person 4. The information output system 100 executes the process of S11 to S14 at any time. The person 4 can confirm the output information on the blood vessel state of the leg using the terminal device 2. That is, when a blood vessel of the leg is determined to be abnormal, the person 4 can notice the abnormality via the screen images as shown in FIGS. 7-9.

As described above in detail, the information output device 1 acquires the first information on the state of the one leg of the person 4 and the second information on another part of the person 4 using the first sensor 31 and the second sensor 32, and determines the blood vessel state of the leg of the person 4 based on the first information and the second information. In addition, the information output device 1 outputs information on the determined blood vessel state to the terminal device 2. Simply by attaching the first sensor 31 and the second sensor 32 to the person 4, it is possible to easily determine and notify of the blood vessel state of the leg of the person 4 without requiring large equipment for diagnosis such as X-ray CT. The person 4 can perform daily actions while wearing the first sensor 31 and the second sensor 32. Therefore, it is possible to routinely determine and notify of the blood vessel state of the leg. Since the determination is routinely executed, an abnormality of a blood vessel can be detected at an early stage when the abnormality occurs, and the abnormality of the blood vessel can be dealt with at an early stage. Therefore, even when the abnormality of the blood vessel occurs, it is possible to prevent deterioration of symptoms.

In the present embodiment, temperatures, t moisture contents, odor intensities, or amounts of carbon dioxide can be used as the first information and the second information. As the abnormality of the blood vessel becomes more severe, the difference in the temperatures, the moisture contents, the odor intensities, or the amounts of carbon dioxide between the leg having the abnormality in the blood vessel and another part becomes larger. Therefore, it is possible to detect the abnormality in the blood vessel of the leg of the person 4 based on the difference in the first information and the second information, and it is possible to easily determine the degree of abnormality of the blood vessel or the progress degree of calcification of the blood vessel.

In the present embodiment, the information output device 1 acquires, using the third sensor 33, the third information such as an acceleration that changes when the person 4 moves compared to when the person 4 is at rest, determines whether the person 4 is in the rest state using the third information, and determines the blood vessel state of the leg when the person 4 is in the rest state. In the rest state, the first information and the second information such as temperatures, moisture contents, odor intensities, or amounts of carbon dioxide are stable. When the person 4 is in the rest state, the stable first information and second information are acquired, and a determination result based on the first information and the second information is less likely to be affected by conditions other than the blood vessel state of the leg of the person 4. Therefore, it is possible to correctly determine the blood vessel state of the leg of the person 4.

In the present embodiment, the terminal device 2 displays an image having a color corresponding to the degree of abnormality or the progress degree of calcification of the blood vessel. When the color changes according to the degree of abnormality or the progress degree of calcification of the blood vessel, an impression received by the person 4 who confirms the output information is changed, and it is possible to cause the person 4 to recognize important information. For example, when the degree of abnormality or the progress degree of calcification of the blood vessel is severe, it is possible to cause the person 4 to recognize that a situation is serious by using a more impressive color. In addition, by outputting advice information corresponding to the blood vessel state of the leg of the person 4, an action to be performed by the person 4 is indicated, and progression of the abnormality of the blood vessel can be prevented.

Second Embodiment

Figure 10:
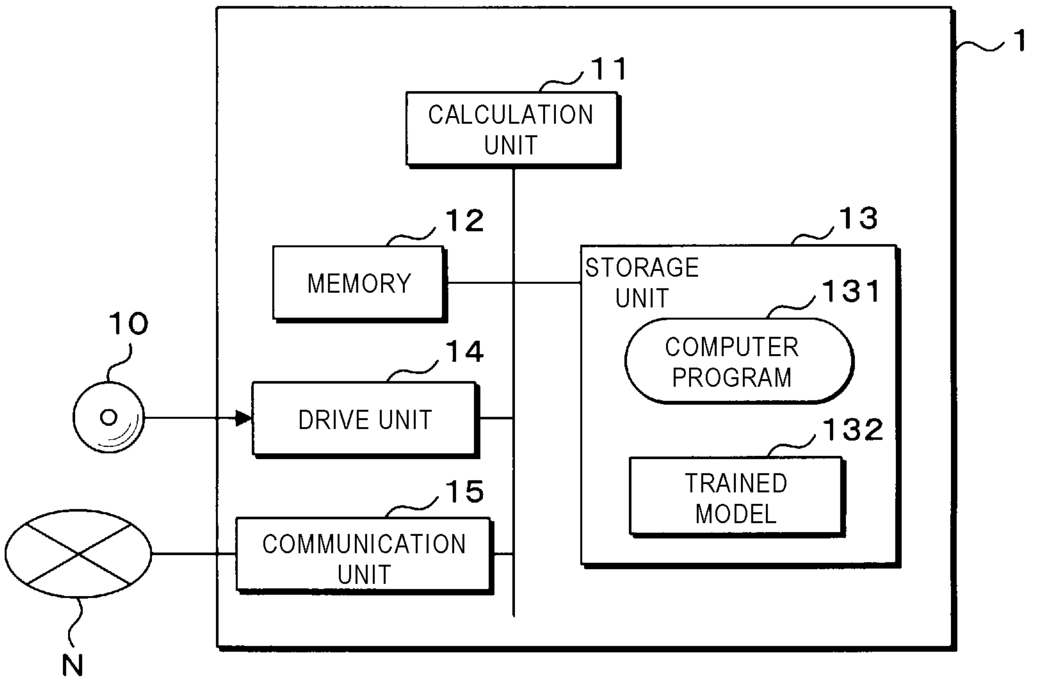
FIG. 10 is a block diagram illustrating an internal functional configuration of an information output device according to a second embodiment.

FIG. 10 is a block diagram illustrating an internal functional configuration of an information output device 1 according to a second embodiment. The information output device 1 includes a trained model 132 used to determine a blood vessel state of a leg of the person 4 based on first information and second information. The trained model 132 is implemented as a computer program 131 executed by the calculation unit 11. The storage unit 13 stores s data necessary for implementing the trained model 132. The trained model 132 may be implemented by hardware. For example, the trained model 132 may be implemented by hardware that includes a processor and a memory storing necessary programs and data. Alternatively, the trained model 132 may be implemented by a quantum processor. Alternatively, the trained model 132 may be provided outside the information output device 1, and the information output device 1 may execute processing using the external trained model 132. Configurations and functions of other portions of the information output device 1 are the same as those in the first embodiment. In addition, configurations and functions of units other than the information output device 1 of the information output system 100 are the same as those in the first embodiment.

Figure 11:
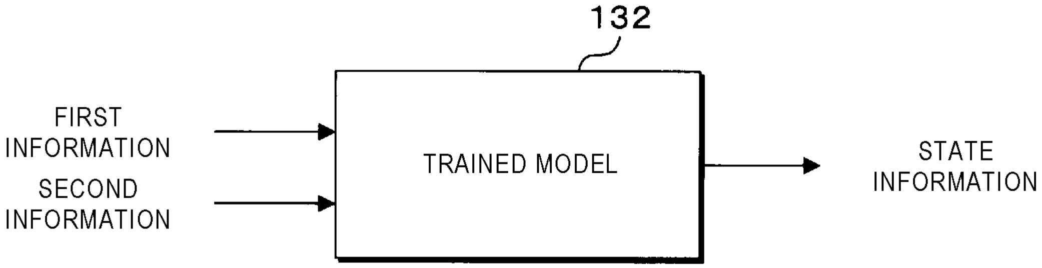
FIG. 11 is a schematic diagram illustrating functions of a trained model.

FIG. 11 is a schematic diagram illustrating functions of the trained model 132. The first information and the second information are input in the trained model 132. The trained model 132 is trained in advance so as to output state information related to the blood vessel state of the leg of the person 4 when the first information and the second information are input. The state information indicates the blood vessel state of the leg of the person 4. The state information may be information indicating a degree of abnormality or a progress degree of calcification of the blood vessel. For example, the trained model 132 may be implemented by a neural network. The trained model 132 may be a model using a method other than the neural network.

Figure 12:
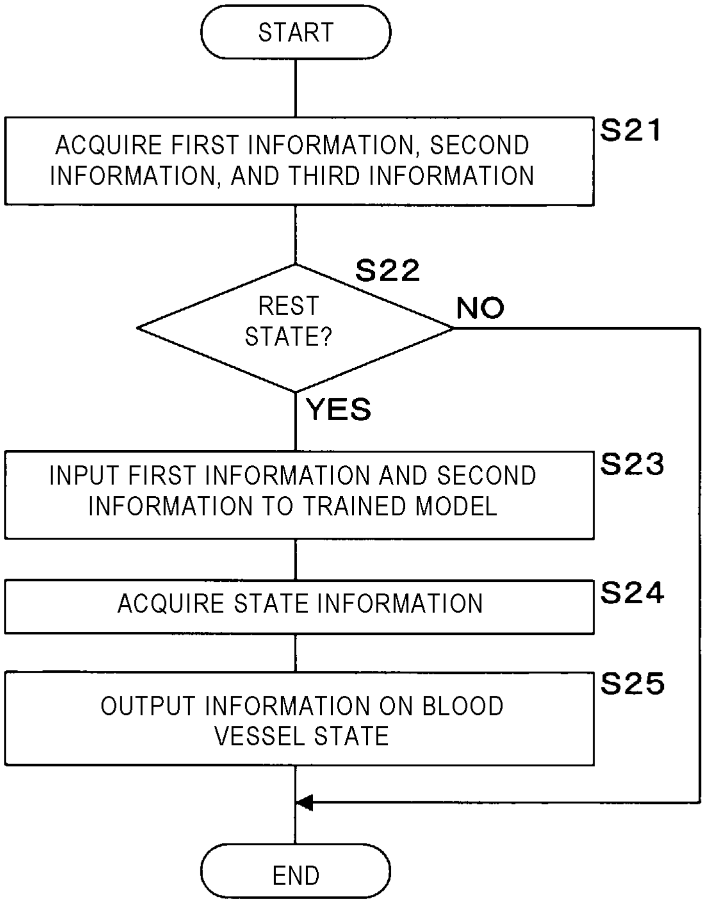
FIG. 12 is a flowchart of an information output process executed by an information output system according to the second embodiment.

FIG. 12 is a flowchart of an information output process executed by the information output system 100 according to the second embodiment. As in the first embodiment, the information output device 1 acquires the first information, the second information, and third information (S21), and determines whether a state of the person 4 is a rest state based on the third information (S22). When the state of the person 4 is not the rest state (S22: NO), the information output device 1 ends the process.

When the state of the person 4 is the rest state (S22: YES), the information output device 1 inputs the first information and the second information to the trained model 132 (S23). In S23, the calculation unit 11 inputs the first information and the second information to the trained model 132. The trained model 132 outputs state information related to the blood vessel state of the leg of the person 4 according to the input of the first information and the second information. The information output device 1 acquires the state information output by the trained model 132 (S24). In S24, the calculation unit 11 determines the blood vessel state of the leg of the person 4 by acquiring the state information.

The information output device 1 may determine the blood vessel state of the leg of the person 4 based on the first information and the second information measured a plurality of times. For example, an average value of a plurality of pieces of the first information and an average of a plurality of pieces of the second information that are acquired within a predetermined length of time are input to the trained model 132. For example, the trained model 132 is trained in advance so as to output state information when a series of the first information and the second information are input. In this aspect, in S23, the calculation unit 11 inputs the series of the first information and the time series of the second information to the trained model 132.

The information output device 1 may determine the blood vessel state of the leg of the person 4 by using the third information in addition to the first information and the second information. In this aspect, the trained model 132 is trained in advance so as to output the state information when the third information is input in addition to the first information and the second information. In this aspect, the processing of S22 is omitted, and determination according to an activity state of the person 4 may be executed.

The first information and the second information may be information indicating any one type of values, such as temperatures, moisture contents, odor intensities, amounts of carbon dioxide, or colors of skin, and may be information indicating a plurality of types of values. In the aspect in which the first information and the second information indicating a plurality of types of values are used, the trained model 132 is trained in advance so as to output state information when the first information and the second information indicating a plurality of types of values are input. In S23, the calculation unit 11 inputs the first information and the second information indicating a plurality of types of values to the trained model 132.

The information output device 1 may determine the blood vessel state of the leg of the person 4 using other information on a state of the leg of the person 4 in addition to the first information and the second information. In this aspect, the trained model 132 is trained in advance so as to output the state information when the other information on the state of the leg of the person 4 is input in addition to the first information and the second information. For example, a fourth sensor that measures a moisture content, an odor intensity, an amount of carbon dioxide, or a color of skin is attached to the leg of the person 4 in addition to the first sensor 31 and the second sensor 32 that measure the temperatures. In S21, information indicating a value measured by the fourth sensor is acquired in addition to the first information, the second information, and the third information. In S24, the calculation unit 11 inputs the information indicating the value measured by the fourth sensor to the trained model 132 in addition to the first information and the second information. In this aspect, the information output device 1 can more correctly determine the blood vessel state of the leg of the person 4 by using the other information on the state of the leg of the person 4.

The information output device 1 may determine the blood vessel state of the leg of the person 4 according to a medical history of the person 4. In this aspect, the trained model 132 is trained in advance so as to output the state information on the blood vessel state of the leg of the person 4 when the medical history of the person 4 is input in addition to the first information and the second information. In S23, the calculation unit 11 identifies the medical history of the person 4 in the same manner as in the first embodiment, and inputs the identified medical history, and the first information and the second information to the trained model 132. The trained model 132 outputs state information according to the input of the first information, the second information, and the medical history.

The trained model 132 may be trained so as to output state information when a difference in the first information and the second information is input. In S23, the calculation unit 11 calculates the difference in the first information and the second information, and inputs the calculated difference to the trained model 132. The trained model 132 outputs the state information according to the input of the difference in the first information and the second information. The trained model 132 may be trained so as to output the state information when the medical history and the difference in the first information and the second information are input.

After S24 is ended, the information output device 1 outputs information on the blood vessel state according to the state information (S25). In S25, the calculation unit 11 transmits the state information from the communication unit 15 to the terminal device 2. The terminal device 2 receives the state information at the communication unit 26. The calculation unit 21 controls the display unit 25 to display a screen image including information on the blood vessel state indicated by the state information. In S25, the calculation unit 11 may generate image data representing the image including the information on the blood vessel state according to the state information, and transmit the image data from the communication unit 15 to the terminal device 2. The terminal device 2 may display the image including the information on the blood vessel state on the display unit 25 based on the image data. The processing of S25 corresponds to an output unit.

After S25 is ended, the information output system 100 ends the process of outputting the information on the blood vessel state of the leg of the person 4. In this way, the information output system 100 executes an information output method. The information output system 100 executes the process of S21 to S25 at any time.

As described above in detail, in the second embodiment, the information output device 1 uses the trained model 132 to determine the blood vessel state of the leg of the person 4 according to the first information and the second information and to output the information on the determined blood vessel state. By using the trained model 132, it is possible to easily determine the blood vessel state of the leg of the person 4. In the second embodiment, it is also possible to routinely determine the blood vessel state of the leg of the person 4. Therefore, an abnormality of a blood vessel of a leg of the person 4 can be detected at an early stage, the abnormality of the blood vessel can be dealt with at an early stage, and deterioration of symptoms can be prevented.

Third Embodiment

Figure 13:
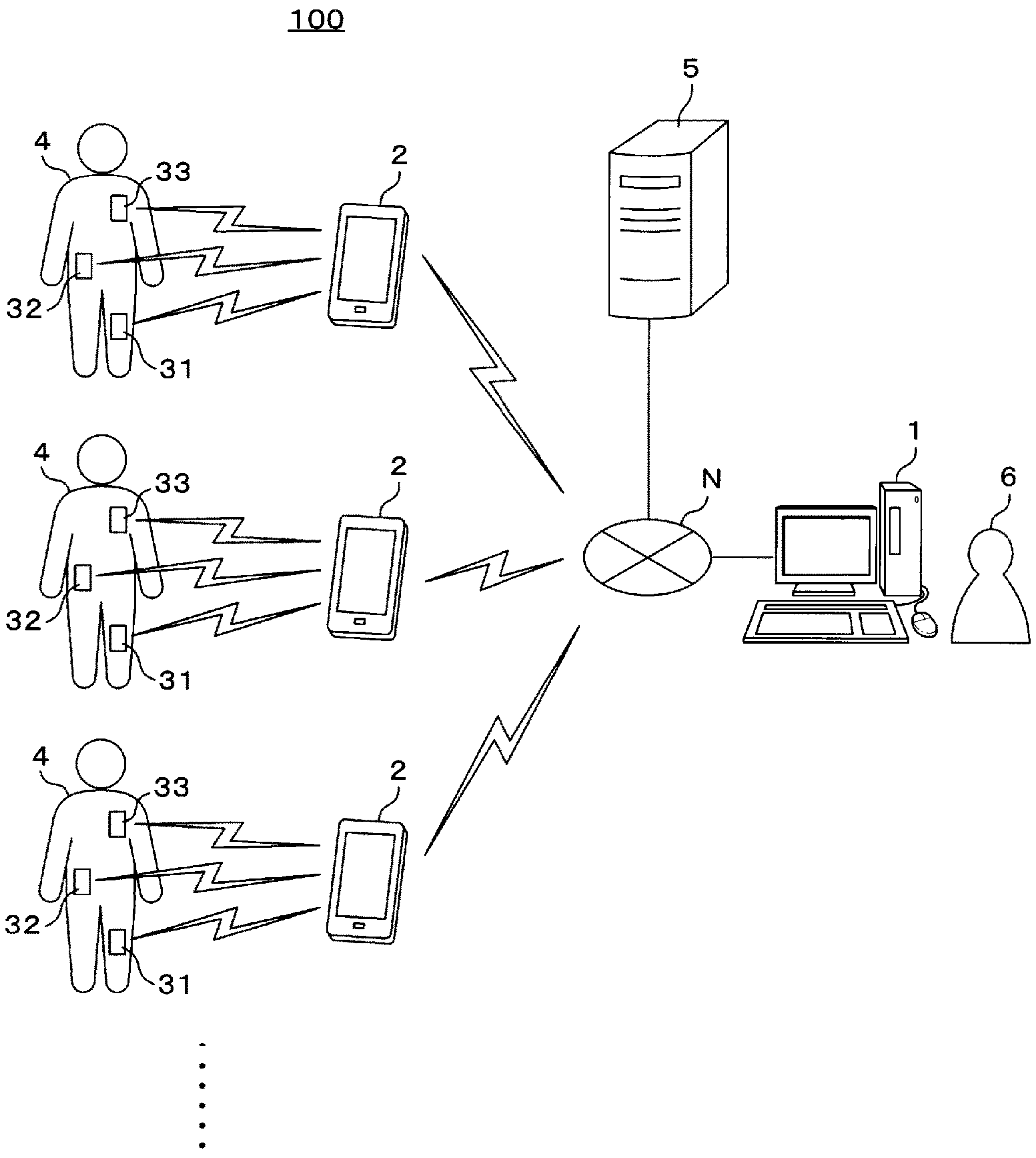
FIG. 13 is a schematic diagram illustrating a configuration of an information output system according to a third embodiment.

FIG. 13 is a schematic diagram illustrating a configuration of an information output system 100 according to a third embodiment. The information output system 100 includes a plurality of sets of a first sensor 31, a second sensor 32, a third sensor 33, and a terminal device 2. First information, second information, and third information are transmitted to an information output device 1 from the first sensor 31, the second sensors 32, and the third sensor 33 that are attached to the body of each person 4 via his or her terminal devices 2 and the communication network N. The information output system 100 includes the information output device 1 and a storage device 5 that are connected to the communication network N. The information output device 1 is operated by an operator 6 such as a medical doctor. The information output system 100 may include a plurality of information output devices 1.

Figure 14:
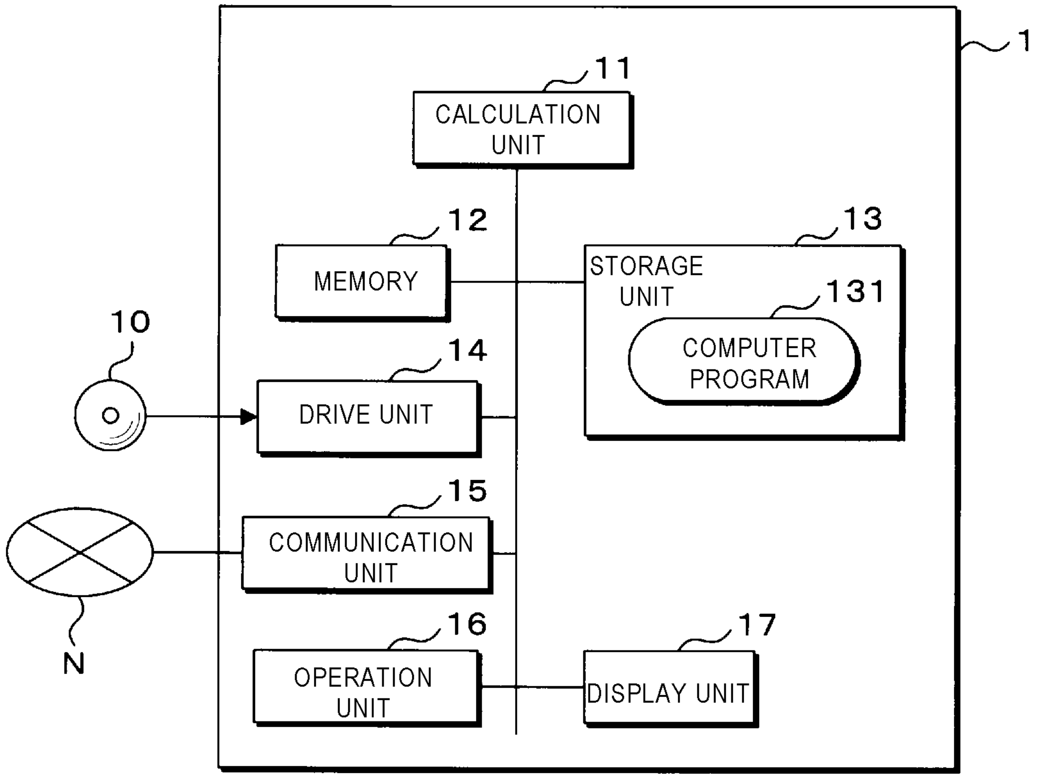
FIG. 14 is a block diagram illustrating an internal functional configuration of an information output device according to the third embodiment.

FIG. 14 is a block diagram illustrating an internal functional configuration of the information output device 1 according to the third embodiment. The information output device 1 includes an operation unit 16 and a display unit 17. The operation unit 16 receives an input operation such as a text input by the operator 6. The operation unit 16 is, for example, a touch panel, a pen tablet, a keyboard, or a pointing device such as a mouse. The display unit 17 displays an image. The display unit 17 is, for example, an LCD or an EL display. The operation unit 16 and the display unit 17 may be integrated into a touch display. Configurations and functions of other portions of the information output device 1 are the same as those in the first embodiment or the second embodiment.

Figure 15:
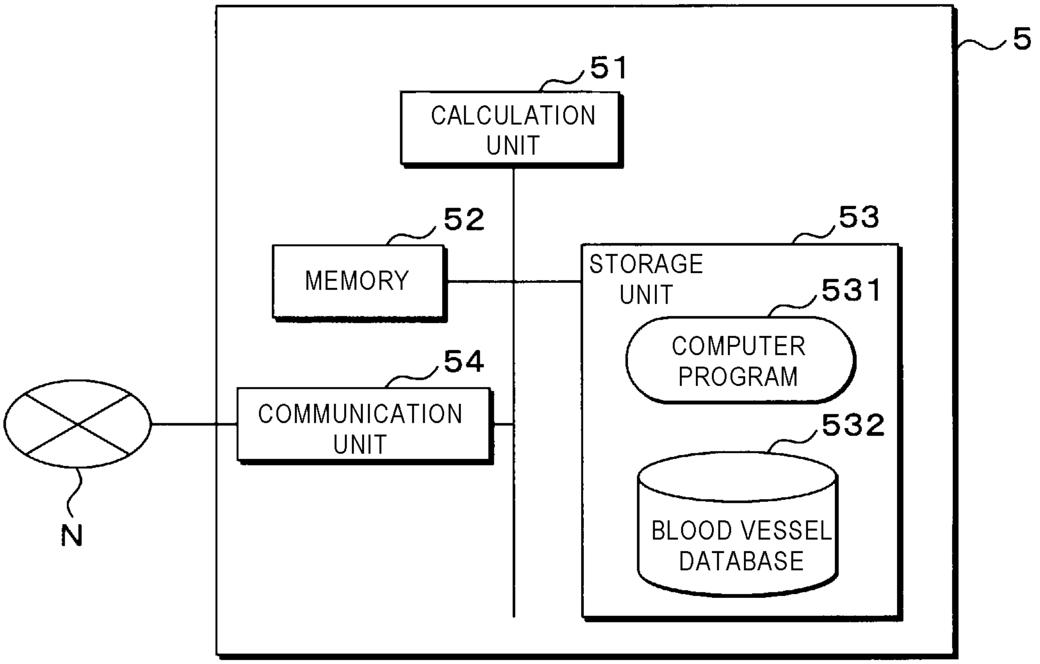
FIG. 15 is a block diagram illustrating an internal functional configuration of a storage device.

FIG. 15 is a block diagram illustrating an internal functional configuration of the storage device 5. The storage device 5 is a computer such as a server device. The storage device 5 includes a calculation unit 51, a memory 52 that stores temporary data generated along with calculation, a storage unit 53, and a communication unit 54. The calculation unit 51 is a processor such as a CPU, a GPU, or a multi-core CPU. The calculation unit 51 may be a quantum processor. The memory 52 is, for example, a RAM. The communication unit 54 is a network interface circuit connectable to the communication network N. The communication unit 54 communicates with the information output device 1 via the communication network N.

The storage unit 53 is nonvolatile, and is, for example, a hard disk. The storage unit 53 stores a computer program 531. The calculation unit 51 executes necessary processing for the storage device 5 according to the computer program 531. In addition, the storage unit 53 stores a blood vessel database 532 in which first information and second information, and information on a blood vessel state of a leg of the person 4 are recorded in association with each other. The storage device 5 may be implemented by a plurality of computers.

The information output system 100 according to the third embodiment executes an information output method in the same manner as in the first embodiment and the second embodiment. That is, the storage unit 13 of the information output device 1 stores threshold data in advance, and the information output system 100 executes the process of S11 to S14. Alternatively, the information output device 1 includes the trained model 132, and the information output system 100 executes the process of S21 to S25.

Figure 16:
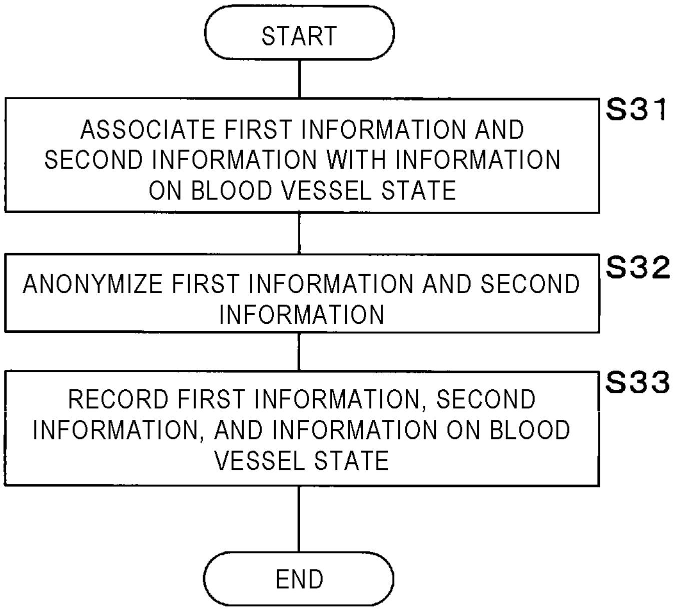
FIG. 16 is a flowchart of an information record process executed by the information output system according to the third embodiment.

After the process of S11 to S14 or S21 to S25 is executed, the information output system 100 executes an information record process of recording the first information and the second information, and the information on the blood vessel state of the leg of the person 4. FIG. 16 is a flowchart of the information record process executed by the information output system 100 according to the third embodiment. The information output device 1 associates the first information and the second information with the information on the blood vessel state (S31). In S31, the calculation unit 11 associates the first information and the second information acquired in the process of S11 to S14 or S21 to S25 with the information on the blood vessel state of the leg of the person 4 determined based on the first information and the second information. The calculation unit 11 may associate information other than the first information and the second information such as a medical history with the information on the blood vessel state.

Next, the information output device 1 anonymizes the first information and the second information (S32). In S32, the calculation unit 11 control the display unit 17 to display the first information, the second information, and information related to the person 4 including the information on the blood vessel state of the leg of the person 4 so that the operator 6 such as a medical doctor operating the operation unit 16 can verify the information. For example, when no discrepancy is present in correlation between the first information and the second information, and the information on the blood vessel state of the leg of the person 4, the operator 6 operates the operation unit 16 to input a verification result indicating that no problem is present to the information output device 1. The calculation unit 11 anonymizes the verified information so that the person 4 cannot be identified. For example, the calculation unit 11 deletes, from the first information, the second information, and the information on the blood vessel state of the leg of the person 4, personal information capable of identifying the person 4.

The information output device 1 records the anonymized first information, second information, and information on the blood vessel state of the leg of the person 4 (S33). In S33, the calculation unit 11 causes the communication unit 15 to transmit the first information and the second information, and the information on the blood vessel state of the leg of the person 4, which are in association with each other and are anonymized, to the storage device 5 via the communication network N. The storage device 5 receives the information transmitted from the information output device 1 on the communication unit 54. The calculation unit 51 records the received first information and second information, and information on the blood vessel state of the leg of the person 4 in the blood vessel database 532 in association with each other. In S32, anonymization may be executed so that the person 4 cannot be identified but the person 4 is the same person, and in S33, information on the same person may be collectively recorded. For example, information acquired a plurality of times for the same person is collectively recorded.

After S33 is ended, the information output system 100 ends the information record process. The information recorded in the blood vessel database 532 is used, for example, as training data for generating the trained model 132 by machine learning. The information output system 100 may include a terminal device used by the operator 6 such as a medical doctor. In S32, the information output device 1 outputs the first information and the second information, and the information related to the person 4 including the information on the blood vessel state of the leg of the person 4 to the terminal device 2 so that the information can be verified by the operator 6 operating the terminal device 2.

As described above in detail, in the third embodiment, the information output system 100 determines the blood vessel state of the leg of the person 4, outputs the determined information on the blood vessel state, and records the first information, the second information, and the information on the blood vessel state of the leg of the person 4 to the blood vessel database 532. The recorded information can be utilized for future medical diagnoses. For example, it is possible to generate and improve the trained model 132 by machine learning using the information recorded in the blood vessel database 532 as the training data and to correctly determine the blood vessel state of the leg of the person 4 using the trained model 132.

In the first to third embodiments, information is transmitted from the first sensor 31, the second sensor 32, and the third sensor 33 to the information output device 1 via the terminal device 2. The first sensor 31, the second sensor 32, and the third sensor 33 may transmit the information to the information output device 1 without passing through the terminal device 2. In the first to third embodiments, the information on the blood vessel state of the leg of the person 4 is displayed on the terminal device 2 possessed by the person 4. The information output system 100 may display the information on the blood vessel state of the leg of the person 4 on an information process device other than the terminal device 2 possessed by the person 4. For example, the information on the blood vessel state of the leg of the person 4 may be displayed on a terminal device used by a medical doctor or a terminal used by a guardian of the person 4. In the first to third embodiments, the third sensor 33 is used, while the information output system 100 may not use the third sensor 33. For example, in the process of S11 to S14 or S21 to S25, processing in which processing using the third information is omitted may be executed. In the first to third embodiments, the blood vessel state of the leg is determined when the person 4 is in the rest state, while the information output device 1 may determine the blood vessel state of the leg when the person 4 is exercising.

The invention is not limited to the above-described embodiments, and various modifications can be made within the scope of the claims. That is, embodiments obtained by combining technical means appropriately modified within the scope of the claims are also included in the technical scope of the invention.

What is claimed is:

1. A non-transitory computer readable medium storing a program for monitoring a health status of a person, wherein the program executed on a computer causes the computer to execute a method comprising:

repeatedly acquiring over time, from a first temperature sensor attached to one leg of the person, a first temperature of said one leg of the person;

repeatedly acquiring over time, from a second temperature sensor attached to a part of a body of the person other than said one leg of the person, a second temperature of the part of the body;

repeatedly acquiring over time, from a motion sensor attached to the body of the person, motion information indicating a motion of the person, the motion information being acquired concurrently with the first and second temperatures;

determining whether the person is in a rest state based on the motion information; and upon determining that the person is in the rest state based on the motion information acquired at a particular time point, determining a progress degree of calcification of a blood vessel in said one leg of the person by comparing a difference between the first and second temperatures acquired at a time closest to the particular time point to a plurality of predetermined thresholds, and generating image data representing a human-shaped figure in which a color of a leg of the human-shaped figure is set based on the difference between the first and second temperatures, and transmitting the image data and information indicating the determined progress degree of calcification of the blood vessel to a mobile terminal that is configured to display the human-shaped figure together with information indicating the progress degree of calcification as the health status of the person, wherein the health status of the person displayed on the mobile terminal is updated based on the image data and the information indicating the progress degree of calcification of the blood vessel.

2. The non-transitory computer readable medium according to claim 1, wherein determining the progress degree of calcification of the blood vessel further comprises inputting the difference between the first and second temperatures acquired at the time closest to the particular time point to a computer model, the computer model having been trained with differences between temperatures acquired from first and second temperature sensors for various persons and a progress degree of calcification of the blood vessel of each of the various persons.

3. The non-transitory computer readable medium according to claim 1, wherein the information indicating the progress degree of calcification of the blood vessel includes voice data indicating a medical advice corresponding to the progress degree of calcification of the blood vessel.

4. The non-transitory computer readable medium according to claim 1, wherein the method further comprises acquiring information indicating a medical history of the person, and the progress degree of calcification of the blood vessel is determined further based on the medical history.

5. The non-transitory computer readable medium according to claim 1, wherein the method further comprises storing in a database the information indicating the determined progress degree of calcification of the blood vessel in association with the first and second temperatures so as not to include personal information of the person.

6. The non-transitory computer readable medium according to claim 1, wherein repeatedly acquiring over time the first temperature includes measuring, by the first temperature sensor, the first temperature at a predetermined sampling interval, repeatedly acquiring over time the second temperature includes measuring, by the second temperature sensor, the second temperature at the predetermined sampling interval, repeatedly acquiring over time the motion information includes measuring, by the motion sensor, the motion information at the predetermined sampling interval, and the method further comprises:

storing a history of the first temperatures, a history of the second temperatures, and a history of the motion information, each measurement of the first temperature, the second temperature, and the motion information being stored in association with a time point at which the measurement is performed.

7. The non-transitory computer readable medium according to claim 1, wherein determining whether the person is in a rest state includes:

calculating an absolute value of an acceleration indicated by the motion information, or an absolute value of a difference among a plurality of accelerations indicated by a plurality of pieces of the motion information acquired within a predetermined length of time, and determining that the person is in the rest state when the calculated absolute value is equal to or less than a predetermined reference value.

8. The non-transitory computer readable medium according to claim 1, wherein the color of the leg of the human-shaped figure is set to a first color when the first temperature is lower than the second temperature, and is set to a second color different from the first color when the first temperature is higher than the second temperature.

9. A method of monitoring a health status of a person, the method comprising:

repeatedly acquiring over time, from a first temperature sensor attached to one leg of the person, a first temperature of said one leg of the person;

repeatedly acquiring over time, from a second temperature sensor attached to a part of a body of the person other than said one leg of the person, a second temperature of the part of the body;

repeatedly acquiring over time, from a motion sensor attached to the body of the person, motion information indicating a motion of the person, the motion information being acquired concurrently with the first and second temperatures;

determining whether the person is in a rest state based on the motion information; and upon determining that the person is in the rest state based on the motion information acquired at a particular time point, determining a progress degree of calcification of a blood vessel in said one leg of the person by comparing a difference between the first and second temperatures acquired at a time closest to the particular time point to a plurality of predetermined thresholds, and generating image data representing a human-shaped figure in which a color of a leg of the human-shaped figure is set based on the difference between the first and second temperatures, and transmitting the image data and information indicating the determined progress degree of calcification of the blood vessel to a mobile terminal that is configured to display the human-shaped figure together with information indicating the progress degree of calcification as the health status of the person, wherein the health status of the person displayed on the mobile terminal is updated based on the image data and the information indicating the progress degree of calcification of the blood vessel.

10. The method according to claim 9, wherein determining the progress degree of calcification of the blood vessel further comprises inputting the difference between the first and second temperatures acquired at the time closest to the particular time point to a computer model, the computer model having been trained with differences between temperatures acquired from first and second temperature sensors for various persons and a progress degree of calcification of the blood vessel of each of the various persons.

11. The method according to claim 9, wherein the information indicating the progress degree of calcification of the blood vessel includes voice data indicating a medical advice corresponding to the progress degree of calcification of the blood vessel.

12. The method according to claim 9, further comprising:

acquiring information indicating a medical history of the person, wherein the progress degree of calcification of the blood vessel is determined further based on the medical history.

13. The method according to claim 9, further comprising:

storing in a database the information indicating the determined progress degree of calcification of the blood vessel in association with the first and second temperatures so as not to include personal information of the person.

14. The method according to claim 9, wherein repeatedly acquiring over time the first temperature includes measuring, by the first temperature sensor, the first temperature at a predetermined sampling interval, repeatedly acquiring over time the second temperature includes measuring, by the second temperature sensor, the second temperature at the predetermined sampling interval, repeatedly acquiring over time the motion information includes measuring, by the motion sensor, the motion information at the predetermined sampling interval, and the method further comprises:

storing a history of the first temperatures, a history of the second temperatures, and a history of the motion information, each measurement of the first temperature, the second temperature, and the motion information being stored in association with a time point at which the measurement is performed.

15. The method according to claim 9, wherein determining whether the person is in a rest state includes:

calculating an absolute value of an acceleration indicated by the motion information, or an absolute value of a difference among a plurality of accelerations indicated by a plurality of pieces of the motion information acquired within a predetermined length of time, and determining that the person is in the rest state when the calculated absolute value is equal to or less than a predetermined reference value.

16. The method according to claim 9, wherein the color of the leg of the human-shaped figure is set to a first color when the first temperature is lower than the second temperature, and is set to a second color different from the first color when the first temperature is higher than the second temperature.

17. A non-transitory computer readable medium storing a program for monitoring a health status of a person, wherein the program executed on a computer causes the computer to execute a method comprising:

repeatedly acquiring over time, from a first sensor attached to one leg of the person, a first odor intensity of said one leg of the person;

repeatedly acquiring over time, from a second sensor attached to a part of a body of the person other than said one leg of the person, a second odor intensity of the part of the body;

repeatedly acquiring over time, from a motion sensor attached to the body of the person, motion information indicating a motion of the person, the motion information being acquired concurrently with the first and second odor intensities;

determining whether the person is in a rest state based on the motion information; and upon determining that the person is in the rest state based on the motion information acquired at a particular time point, determining a progress degree of calcification of a blood vessel in said one leg of the person by comparing a difference between the first and second odor intensities acquired at a time closest to the particular time point to a plurality of predetermined thresholds, and generating image data representing a human-shaped figure in which a color of a leg of the human-shaped figure is set based on the difference between the first and second odor intensities, and transmitting the image data and information indicating the determined progress degree of calcification of the blood vessel to a mobile terminal that is configured to display the human-shaped figure together with information indicating the progress degree of calcification as the health status of the person, wherein the health status of the person displayed on the mobile terminal is updated based on the image data and the information indicating the progress degree of calcification of the blood vessel.

* * * * *